United States Patent [19]
Margolin

[11] Patent Number: 6,090,822
[45] Date of Patent: Jul. 18, 2000

[54] TREATMENT OF CYTOKINE GROWTH FACTOR CAUSED DISORDERS

[76] Inventor: Solomon B. Margolin, 6723 Desco Dr., Dallas, Tex. 75225

[21] Appl. No.: 09/162,011

[22] Filed: Sep. 28, 1998

Related U.S. Application Data

[63] Continuation-in-part of application No. 08/913,202, Sep. 3, 1997, abandoned, which is a continuation of application No. PCT/US96/02737, Mar. 4, 1996, which is a continuation-in-part of application No. 08/397,962, Mar. 3, 1995, abandoned.

[51] Int. Cl.⁷ .......................... A61K 31/44; A61K 31/47
[52] U.S. Cl. .......................... 514/313; 514/334; 514/336; 514/341; 514/342; 514/345
[58] Field of Search ............................... 514/345, 336, 514/334, 341, 342, 313

[56] References Cited

U.S. PATENT DOCUMENTS

| | | | |
|---|---|---|---|
| 4,042,699 | 8/1977 | Gadekar | 514/345 |
| 4,052,509 | 10/1977 | Gadekar | 514/345 |

*Primary Examiner*—Jerome D. Goldberg
*Attorney, Agent, or Firm*—John H. Crozier

[57] ABSTRACT

In preferred embodiments, a method of prevention and treatment of disorders caused by enhanced proliferation and enhanced biosynthesis caused by cytokine growth factors in humans and other animals, the method including: administering to a human or other animal an effective dose of a pharmaceutical substance including an N-substituted 2(1H) pyridone and/or an N-substituted 3(1H) pyridone; and a composition for prevention and treatment of disorders caused by enhanced proliferation and enhanced biosynthesis caused by cytokine growth factors in humans and other animals, the composition including: a pharmaceutical preparation including an effective dose of an N-substituted 2(1H) pyridone and/or an N-substituted 3(1H) pyridone.

4 Claims, 9 Drawing Sheets

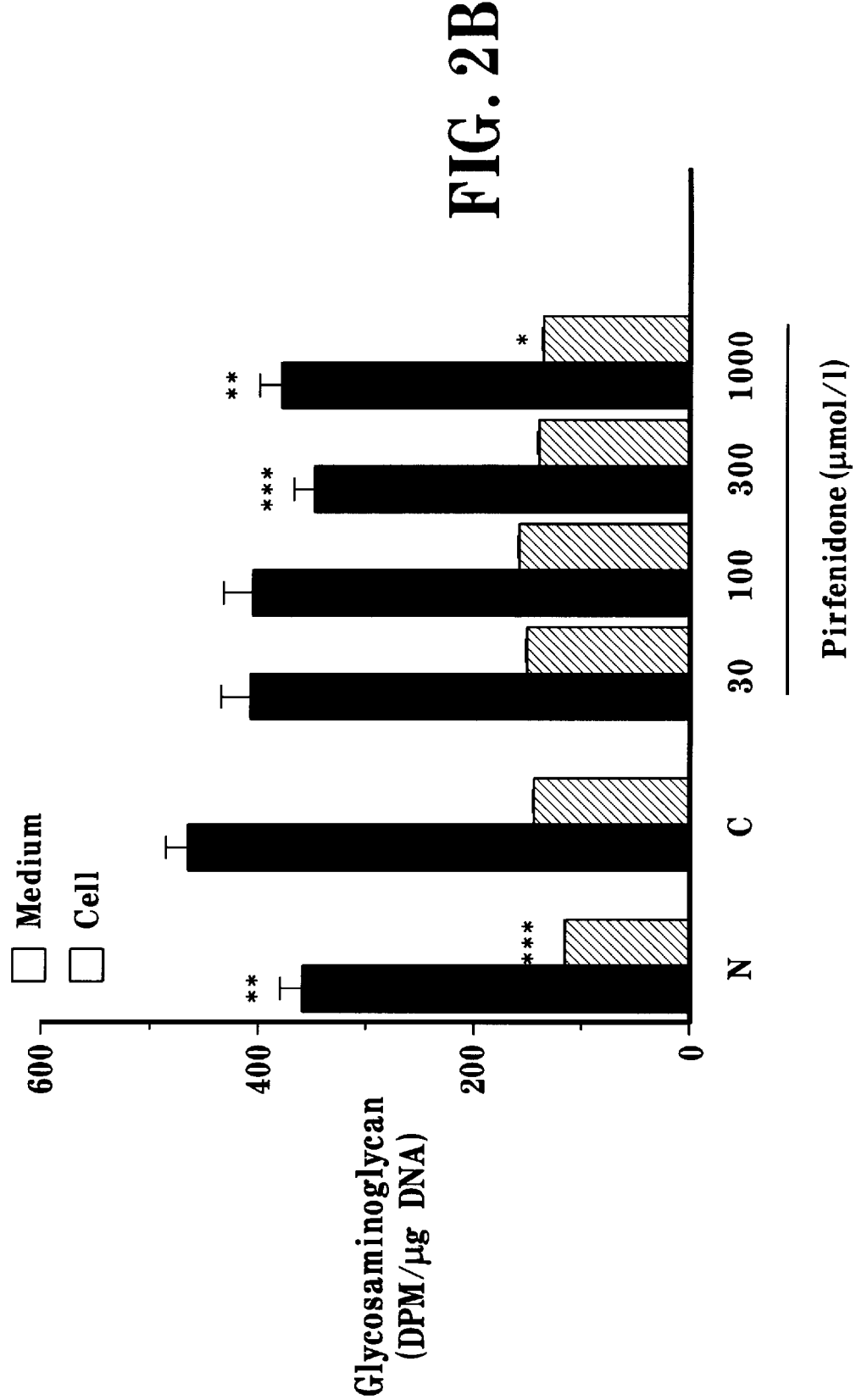

TREATMENT OF CYTOKINE GROWTH FACTOR CAUSED DISORDERS

CROSS-REFERENCE TO RELATED APPLICATIONS

The present application is a continuation-in-part of U.S. application Ser. No. 08/913,202, filed Sep. 3, 1997, abandoned, which is a continuation of Patent Cooperation Treaty Application No. PCT/US96/02737, filed Mar. 4, 1996, which is a continuation-in-part of U.S. application Ser. No. 08/397,962 filed Mar. 3, 1995, abandoned.

BACKGROUND OF THE INVENTION

1. Field of the Invention

The present invention relates to the prevention and treatment of disorders in humans and other animals generally and, more particularly, but not by way of limitation, to compositions and methods for prevention and treatment of disorders caused by enhanced proliferation and enhanced biosynthesis caused by cytokine growth factors.

2. Background Art

The clinical applications for chemical substances (new drugs) which block or inhibit the activity of four cytokine growth factors and their closely related chemical peptides, transforming growth factor (TGF-Beta-1), platelet-derived growth factor (PDGF), epidermal growth factor (EGF), and fibroblast growth factor (FGF), will have extraordinary medicinal applications in the following major proliferative disorders: immunology (allergy, auto-immunity, immunosuppression), fibrotic lesions (all vital organs), infections of virus origin (herpes, Roux virus, etc.), tissue injuries caused by bacterial or fungal infections, and tissue injuries caused by trauma, extravasation from blood vessels or blood vessel rupture with hemorrhage into adjacent tissues, and, finally, occlusions (clots or stenosis) of blood vessels.

Each of the above conditions readily triggers massive proliferation and activation of mesenchymal or mesenchymal-like cells resulting in extensive inflammation, dislocation, and deformities of blood vessels and organ structures. These are visualized and experienced clinically in the form of disabling organ (i.e., lungs, kidneys, skin, joints, cardiac, brain, etc.) dysfunction.

A perspective of the possibilities is seen in the review articles of the role of TGF-Beta-1, along with some reference to the other growth factors as presented by Border and Noble, "Transforming Growth Factor [Beta] in Tissue Fibrosis", *The New England Journal of Medicine,* Nov. 10, 1994, pages 1286–1292; also, Varga and Jimenez, "Modulation of Collagen Gene Expression: Its Relation to Fibrosis in Systemic Sclerosis and Other Disorders", *Annals of Internal Medicine,* Vol. 122, No. 1, January 1995.

Accordingly, it is a principal object of the present invention to provide compositions and methods for prevention and treatment of disorders caused by enhanced proliferation and enhanced biosynthesis caused by cytokine growth factors.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in preferred embodiments, a method of prevention and treatment of disorders caused by enhanced proliferation and enhanced biosynthesis caused by cytokine growth factors in humans and other animals, comprising: administering to a human or other animal an effective dose of a pharmaceutical substance including an N-substituted 2(1H) pyridone and/or an N-substituted 3(1H) pyridone; and a composition for prevention and treatment of disorders caused by enhanced proliferation and enhanced biosynthesis caused by cytokine growth factors in humans and other animals, comprising: a pharmaceutical preparation including an effective dose of an N-substituted 2(1H) pyridone and/or an N-substituted 3(1H) pyridone.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Figure 1A:
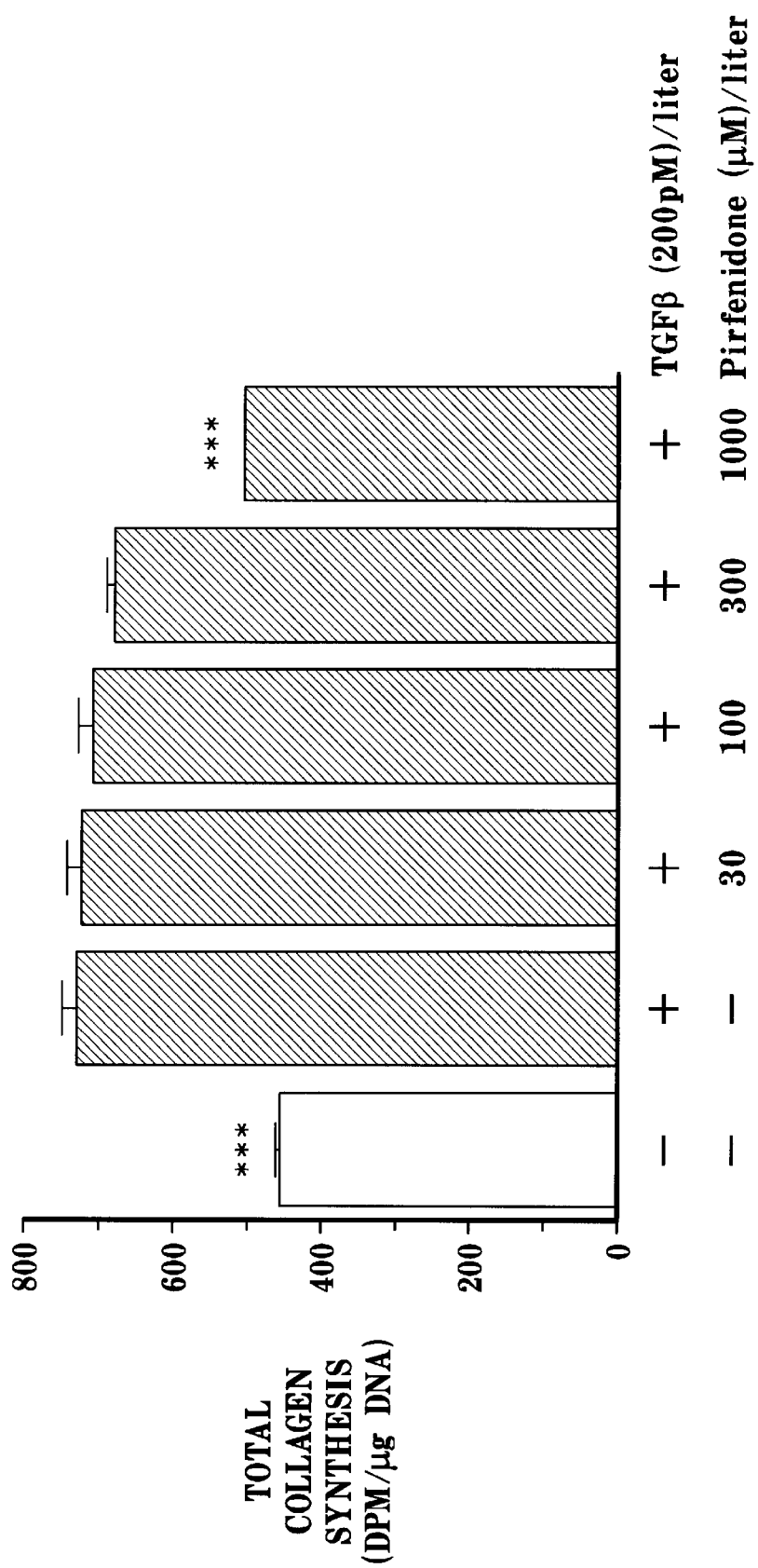
FIGS. 1A–6 illustrate the effects of prevention and treatment with pirfenidone of disorders caused by cytokine growth factors in humans and other animals.

5-Methyl-1-phenyl-2-(1H)-pyridone, "pirfenidone", and related substances inhibit the proliferation and activating actions of the aforementioned four growth factors and as a result, prevent or correct the lesions generated in the above cited categories: immunology (allergy, auto-immunity, immunosuppression), fibrotic lesions (all vital organs), infections of virus origin (herpes, Roux virus, etc.), tissue injuries caused by bacterial or fungal infections, and tissue injuries caused by trauma, extravasation from blood vessels or blood vessel rupture with hemorrhage into adjacent tissues, and, finally, occlusions (clots or stenosis) of blood vessels. Pirfenidone and related drugs inhibit these pathogenic actions in a pharmacological manner at doses which are much smaller than those which produce toxic effects in in vitro tissue cultures and living animals or humans.

Some details of the roles that these four growth factors play in the cited pathogenesis are described in the following paragraphs:

In the pathogenesis of proliferative diseases, excessive cell proliferation occurs as a result of the presence of various cytokine growth factors, such as TGF-Beta-1 platelet-derived growth factor (PDGF), epidermal growth factors (EGF), and fibroblast growth factor (FGF). For example, growth factors produced by cellular constituents in the blood, and by the damaged arterial vessel wall mediate the proliferation of smooth muscle cells in vascular restenosis.

Other cytokines growth factors involved with TGF-Beta-1 in tissue remodeling after injury are platelet derived growth factor (PDGF) and basic fibroblast growth factor (bFGF). Each cytokine has distinctive, synergistic roles in tissue repair, as recent studies involving in vivo gene transfection, gene disruption ("knockout"), and the administration of cytokines have shown. Excessive cellular proliferation may be induced by cytokines such as FGF-Beta-1 platelet-derived growth factor (PDGF), epidermal growth factor (EGF), and/or fibroblast growth factor (TGF).

A central event in tissue repair is the release of cytokines in response to injury. Transforming growth factor B (TGF-Beta-1) is a key growth factor that initiates tissue repair and whose sustained production underlies the development of tissue fibrosis (ref. 104, 105). (Copies attached.)

The regulation of TGF-Beta-1 secretion and action involves complex post-transcriptional events, including messenger RNA (mRNA) stabilization, the assembly and activation of the latent TGF-Beta-1 complex, and the modulation of receptor expression.

TGF-Beta-1 is unique in its widespread actions that enhance the deposition of extracellular matrix. It also acts as a potent regulator of repair, coordination or suppressing the actions of other cytokines.

At physiologic concentrations, TGF-Beta-1 regulates PDGF (in smooth-muscle cells and fibroblasts), FGF (in endothelial cells), by stimulating or inhibiting their production or modulating their actions to both synchronize and control the repair process. TGF-Beta-1 consistently and potently acts on cells to induce the deposition of extracellular matrix.

Immunological antagonists of transforming growth factor-Beta-1 prevent fibrosis. For instance, neutralizing anti-transforming growth factor-B antibody inhibited scar formation in healing dermal wounds and prevented the development of carotid initimal hyperplasia after balloon angioplasty.

Measuring Inhibition of Fibroblast Proliferation

1. WI38 cells (50,000 per ml) were grown in 2.0 FBS for 24 hours prior to addition of growth factor; thereafter, cultured for an additional 72 hours. The cells were maintained in 2.0% FBS for the entire experiment.

2. After culturing, 500 microliters of filtered neutral red (10 mg/100 ml) were added for 1 hour.

3. Monolayers were washed twice with warm PBS (saline) to remove excess stain.

4. Adsorbed stain was extracted with a solution containing 50% ethanol in 100 mM $NaH_2PO_4$.

5. 200 microliters were removed from each treatment and added to one well of a 96 well plate.

6. Optical density (O.D.) was read at 550 nm with a Biotek plate reader.

7. Amount of stain retained by cells served as an index of cell growth.

Inhibition of Growth Factor-Enhanced Fibroblast Proliferation

The enhanced proliferation of WI38 fibroblasts after exposure to PDGF (platelet derived growth factor; or FGF (fibroblast growth factor) was blocked by pirfenidone added to cell growth media. Pirfenidone also inhibited the rise in collagen output by WI38 fibroblast cultures when induced by TGF-beta-1 (transforming growth factor-beta-1). The enhanced proliferation of WI38 fibroblasts after exposure to PDGF (platelet derived growth factor) or FGF (fibroblast growth factor was blocked by pirfenidone added to cell growth media.

TABLE 1

INHIBITION BY PIRFENIDONE OF ENHANCED PROLIFERATION INDUCED BY PLATELET DERIVED GROWTH FACTOR (PDGF) IN HUMAN LUNG FIBROBLAST (WI38) CELL CULTURES
Platelet Derived Growth Factor (PDGF)
(1.0 micrograms per ml)

| Plate Treatment | Optical Density |
| --- | --- |
| 1. Control (C) | 0.1278 +/− 0.0015 |
| 2. C + PDGF | 0.1529 +/− 0.0026 |
| 3. 100 mcg pirfenidone (P) | 0.1215 +/− 0.0047 |
| 4. 100 mcg P + PDGF | 0.1129 +/− 0.0041 |
| 5. 300 mcg P | 0.0968 +/− 0.0016 |
| 6. 300 mcg P + PDGF | 0.0934 +/− 0.0036 |

Conclusions:

1. PDGF, 1.0 mcg/ml, significantly INCREASED cell proliferation.

Student's T=8.36; P<0.01

2. Pirfenidone (100 mcgs per ml) alone significantly INHIBITED cell proliferation, but not significantly.

Student's T=1.49; not significant statistically

3. Pirfenidone (300 mcgs per ml) alone significantly INHIBITED cell proliferation.

Student's T=14.1; P<0.01

4. Pirfenidone (100 mcgs per ml) significantly INHIBITED the INCREASED cell proliferation induced by 1.0 mcgs/ml of PDGF.

Student's T=8.16; P<0.01

5. Pirfenidone (300) mcgs per ml) significantly INHIBITED the INCREASED cell proliferation induced by 1.0 mcgs/ml of PDGF.

Student's T=13.2; P<0.01

TABLE 2

INHIBITION BY PIRFENIDONE OF ENHANCED CELL PROLIFERATION INDUCED BY FIBROBLAST GROWTH FACTOR (FGF) IN HUMAN LUNG FIBROBLAST (WI38) CELL CULTURES
(FGF, 0.5 micrograms [mcg] per ml)

| Plate Treatment | Optical Density |
| --- | --- |
| 1. Control (C) | 0.1389 +/− 0.0028 |
| 2. C + FGF | 0.1514 +/− 0.0058 |
| 3. 100 mcg pirfenidone (P) | 0.1206 +/− 0.0039 |
| 4. 100 mcg P + FGF | 0.1018 +/− 0.0036 |
| 5. 300 mcg P | 0.0936 +/− 0.0016 |
| 6. 300 mcg P + FGF | 0.0963 +/− 0.0038 |

Conclusions:

1. FGF, 0.5 mcgs/ml, significantly INCREASED cell proliferation.

Student's T=1.95; P+0.055

2. Pirfenidone (100 mcgs per ml) alone significantly INHIBITED cell proliferation.

Student's T=2.61; P+0.02

3. Pirfenidone (300 mcgs per ml) alone significantly INHIBITED cell proliferation.

Student's T=7.55; P<0.01

4. Pirfenidone (100 mcgs per ml) significantly INHIBITED the INCREASED cell proliferation caused by 0.5 mcgs/ml of FGF.

Student's T=7.29; P<0.01

5. Pirfenidone (300 mcgs per ml) significantly INHIBITED the INCREASED cell proliferation caused by 0.5 mcgs/ml of FGF.

Student's T=7.87; P<0.01

Collagen Purification

1. Media DMEM+10% FBS.

2. Ascorbic acid stock (100×) 5 mg/ml stored frozen, add 500 microliters/5 ml media just prior to use.

3. Prepare 0.025M Tris buffer (3 g/l) at pH 7.5 containing $5×10^{-5}$ (N-ethylmaleimide, Sigma) NEM (1–25 mg/ml).

Collagen in culture media (Use 24-well cluster plate)

1. Set up one 24-well plate using WI38 cells suspended in DMEM+10% FBS+50 micrograms/ml ascorbic acid. Allow cells to grow to confluency in 48–72 hours. Add 0.5 ml media per well.

2. Discard media and add new DMEM without FBS but with ascorbic acid.

| | |
|---|---|
| 6 control wells | 0.5 ml new media |
| 6 pirfenidone wells | Pirfenidone 0.2 mg/ml |
| 6 TGF-beta wells | TGF beta-1 ng/ml |
| 6 TGF-beta + pirfenidone | Pirf. 0.2 mg/ml + TGF beta 1 ng/ml |

3. Add 2 microcuries of 3H Proline to all wells (or add 50 microliters of isotope solution containing 40 microcuries/ml media. Incubate at 37° C. $CO_2$ incubator for 24 hours.

4. Collect medium from each well and dialyze separately (or pools) using dialysis bags against Tris buffer (#3 above) with 3 exchanges every 24 hours.

5. Collect dialysate and divide fluid from each bag into equal 0.3 ml aliquots.

6. Determine total counts of 3H for each well using one of three 0.3 ml aliquots.

7. With remaining two aliquots for each well, treat with or without 2.5 units collagenase (Advance Biofactures) for 18 hours at 37° C. Add 0.6 ml of reaction mixture (0.025M Tris, $5 \times 10^{-5}$ NEM, 1% BAS and 0.02M $CaCl_2$).

8. Stop reaction by adding 200 microliters of solution containing 25% TCA+1.25% tannic acid to precipitate proteins.

9. Centrifuge to remove precipitate and count supernatants in scintillation counter.

10. Express results relative to 3H incorporation in collagen.

Procedure of:
1. Peterofsky B and Diegelmann R., Biochemistry, 10, 988–994, 1971.
2. Russell J. D., Russell S. B., and Trupin K. M., J. Cell Physiology, 97, 221–230, 1978.

Inhibition by Pirfenidone of Growth Factor-Enhanced Synthesis by Fibroblasts of Collagen and GAG

TABLE 3

INHIBITION BY PIRFENIDONE OF ENHANCED COLLAGEN SYNTHESIS INDUCED BY TRANSFORMING GROWTH FACTOR (TGF-B-1)
(Cell cultures of human lung fibroblasts, strain WI38)

| | No. of Wells | Mean |
|---|---|---|
| 1. Control | 6 | 5.63 +/- 0.89 |
| 2. Pirfenidone only | 6 | 3.77 +/- 0.89 |
| 3. TGF-B-1* only | 6 | 10.60 +/- 2.17** |
| 4. TGF-B-1* plus Pirfenidone | 5 | 6.28 +/- 2.13 |

*1.0 nanograms per ml.
**Only group differing significantly from Control (Group #1); P = 0.05.

Note: Cells were grown in PSB-free medium, pirfenidone was added on day 0 and allowed 48–72 hours for cells to grow to confluency. Radioactive proline (2 microcuries per well) was added 6 hours before harvesting.

Figure 1B:
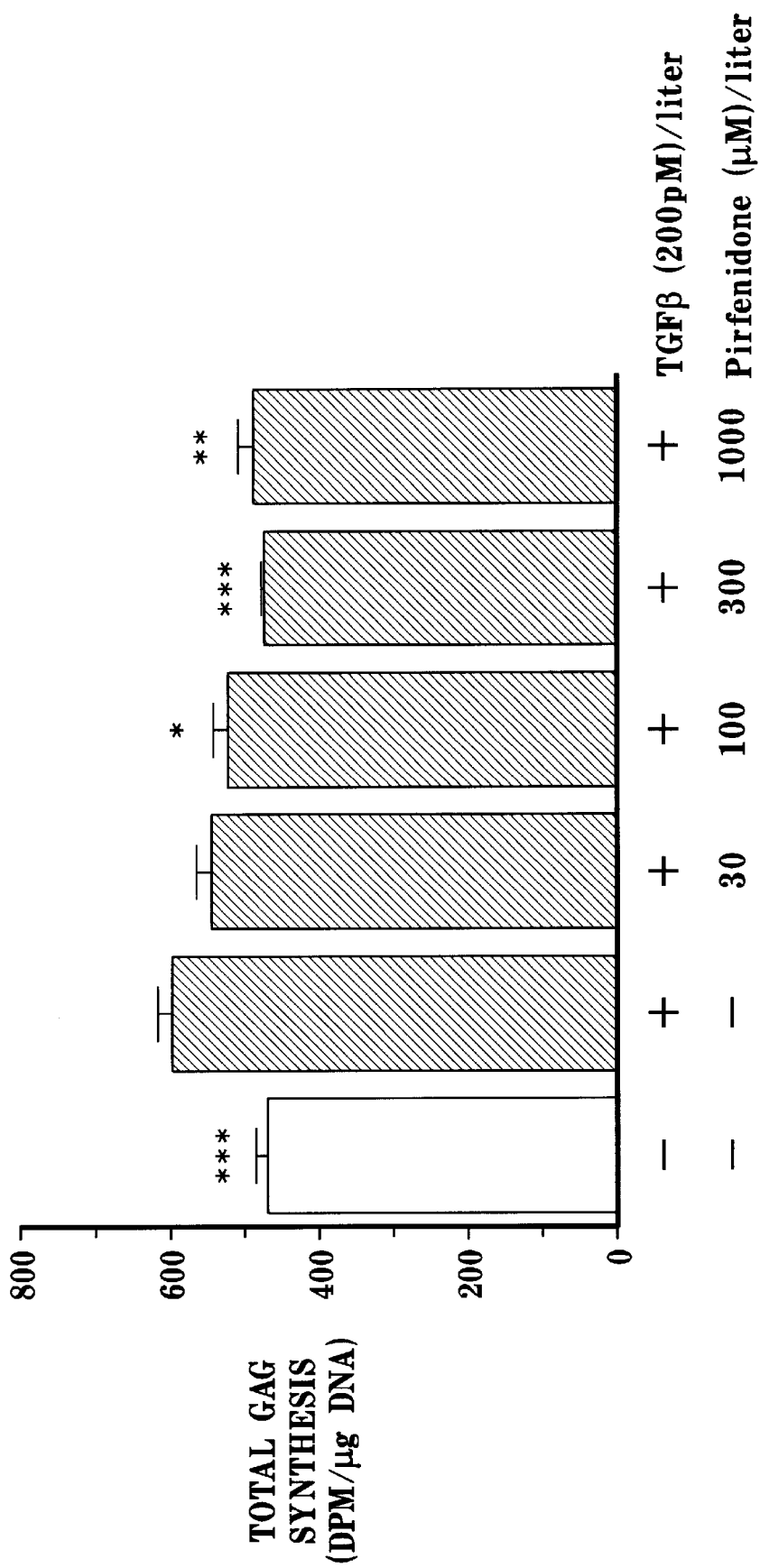

FIGS. 1A and 1B illustrate the effect of pirfenidone on TGF-Beta-enhanced collagen (FIG. 1A) and glycosaminoglycans (GAG) (FIG. 1B) synthesis in cultured human normal dermal fibroblasts. Confluent cells were serum-starved for 24 hours and then treated with TGF-Beta and pirfenidone for 6 hours at the indicated concentrations. Incorporation of 3H proline (for collagen or 35 $SO_4$ (for GAG) into medium and cell lysates were measured as total synthesis. Results: *, , and *, p<0.05, 0.01, and 0.001, respectively, vs. a group treated with TGF-Beta alone (Student's t-test).

Figure 2A:
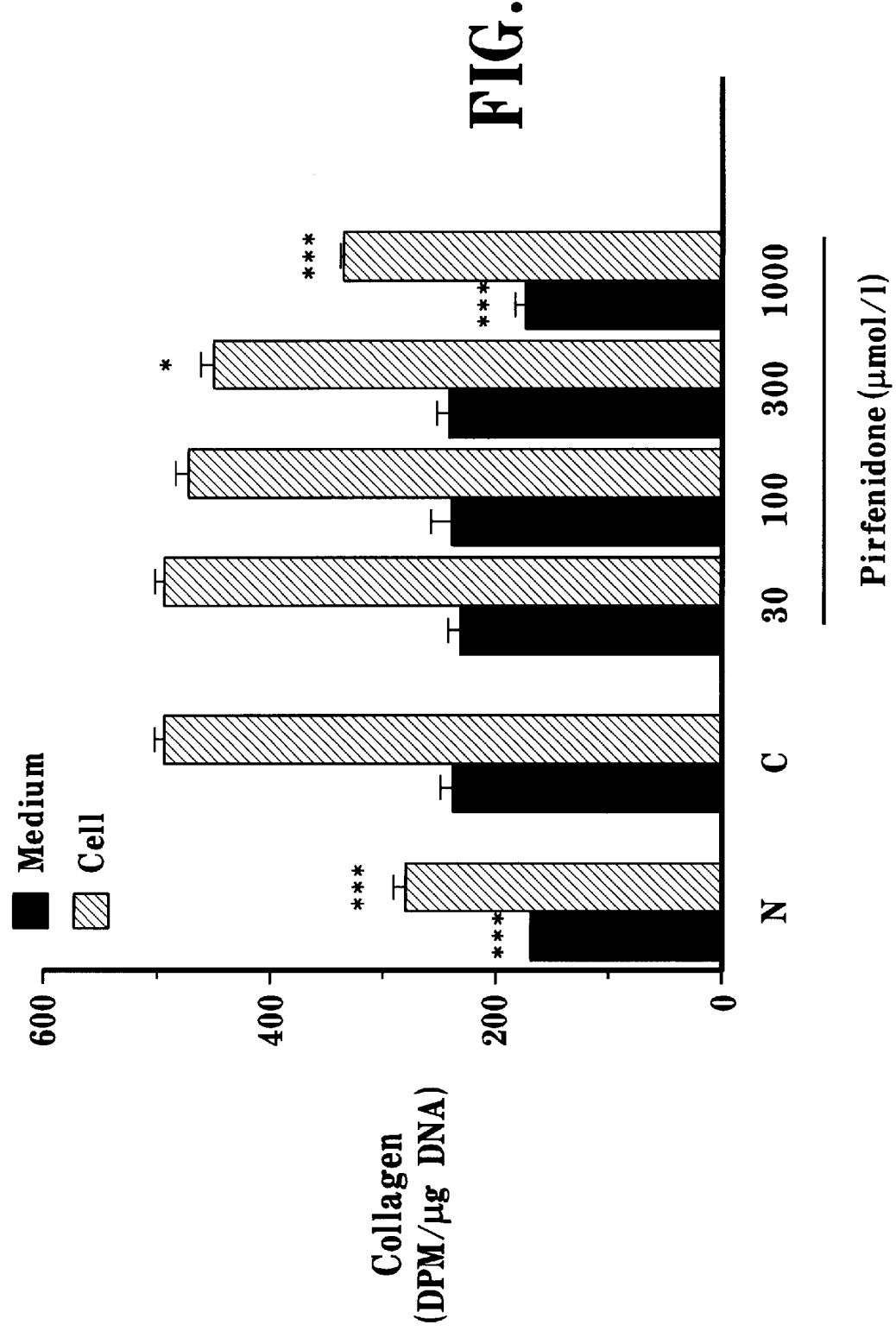

FIGS. 2A and 2B illustrate the effect of pirfenidone on TGF-Beta-1 (200 pmol/l)-enhanced collagen (FIG. 2A) and glycosaminoglycan (FIG. 2B) synthesis in cultured human normal dermal fibroblasts. Each column indicates the mean =/-SE of five experiments. Results: *, , and *, significantly different from the control (C) at p<0, 00.5, 0.01, and 0.001, respectively.

Figure 3:
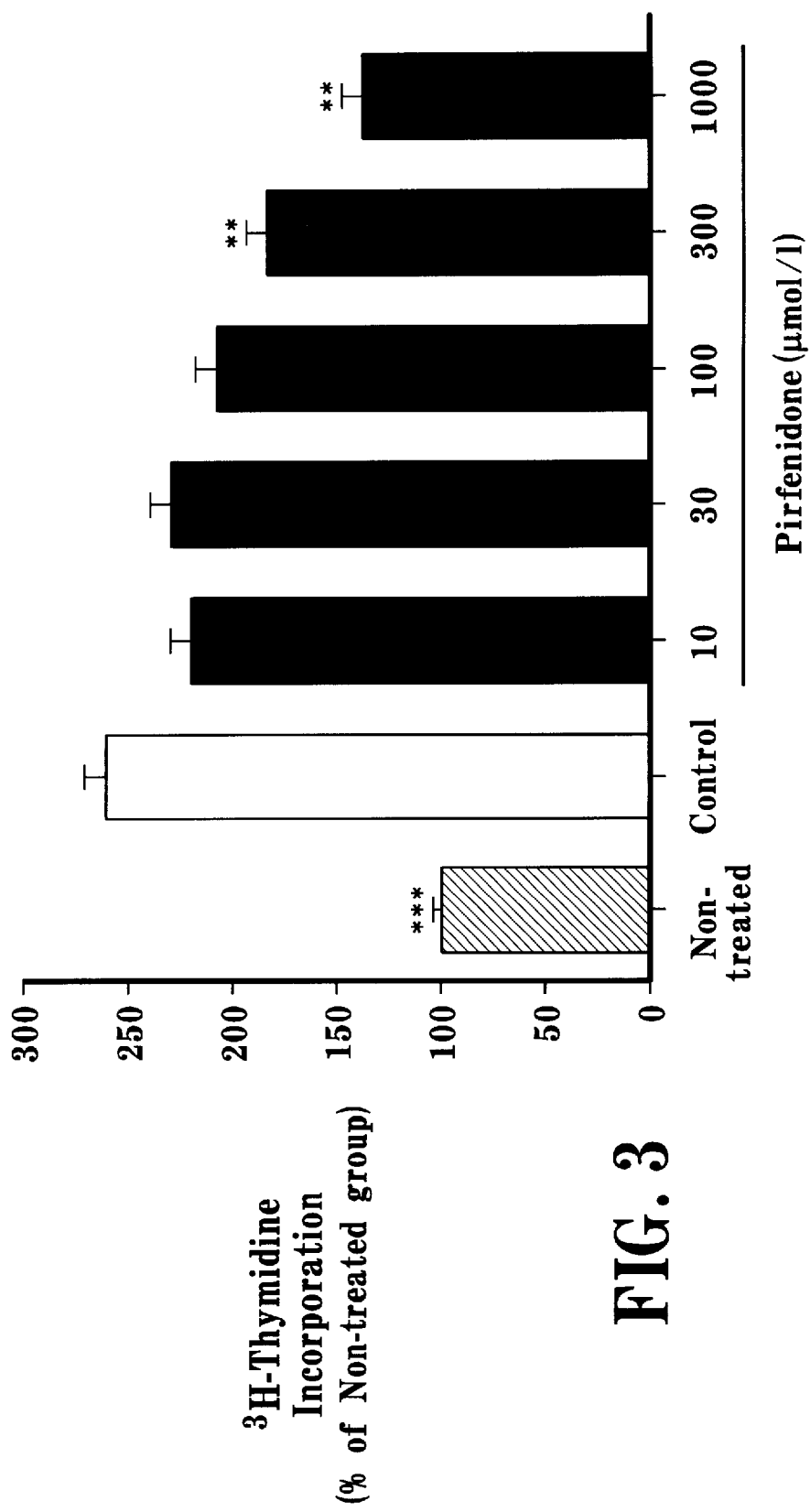

FIG. 3 illustrates the effect of pirfenidone on DNA synthesis of human skin fibroblast stimulated with 10% FBS (A) and PDGF-BB (B). The data is expressed as mean =/-SE of six experiments. Results: *, , and *, significantly different from control at p<0.05, p<0.01, and p<0.001, respectively.

Effect on Collagen Syntheses in Cultured Human Prostate Stromal Cells

Methods

Human hypertrophied prostate was cut into small pieces and digested with 0.1% collagenase, 10% FBS in DMEM for 24 hours. Dispersed cells were collected by centrifugation at 1000 rpm. Suspended cells were centrifuged at 300 rpm and resulting supernatant which contained stromal cells were collected. Stromal cells were cultured in 10% FBS-DMEM. Confluent stromal cells were preincubated in FBS-free medium for 24 hours. and incubated in FBS-free medium containing 25 micrograms/ml of ascorbic acid and 80 micrograms/ml of beta-aminopropionitrile for 24 hours. The conditioned media were collected and the procollagen contents were determined using a procollagen assay kit. Effects of pirfenidone on TGF-beta induced procollagen production were investigated. Assays were performed in triplicate.

Results

Figure 4:
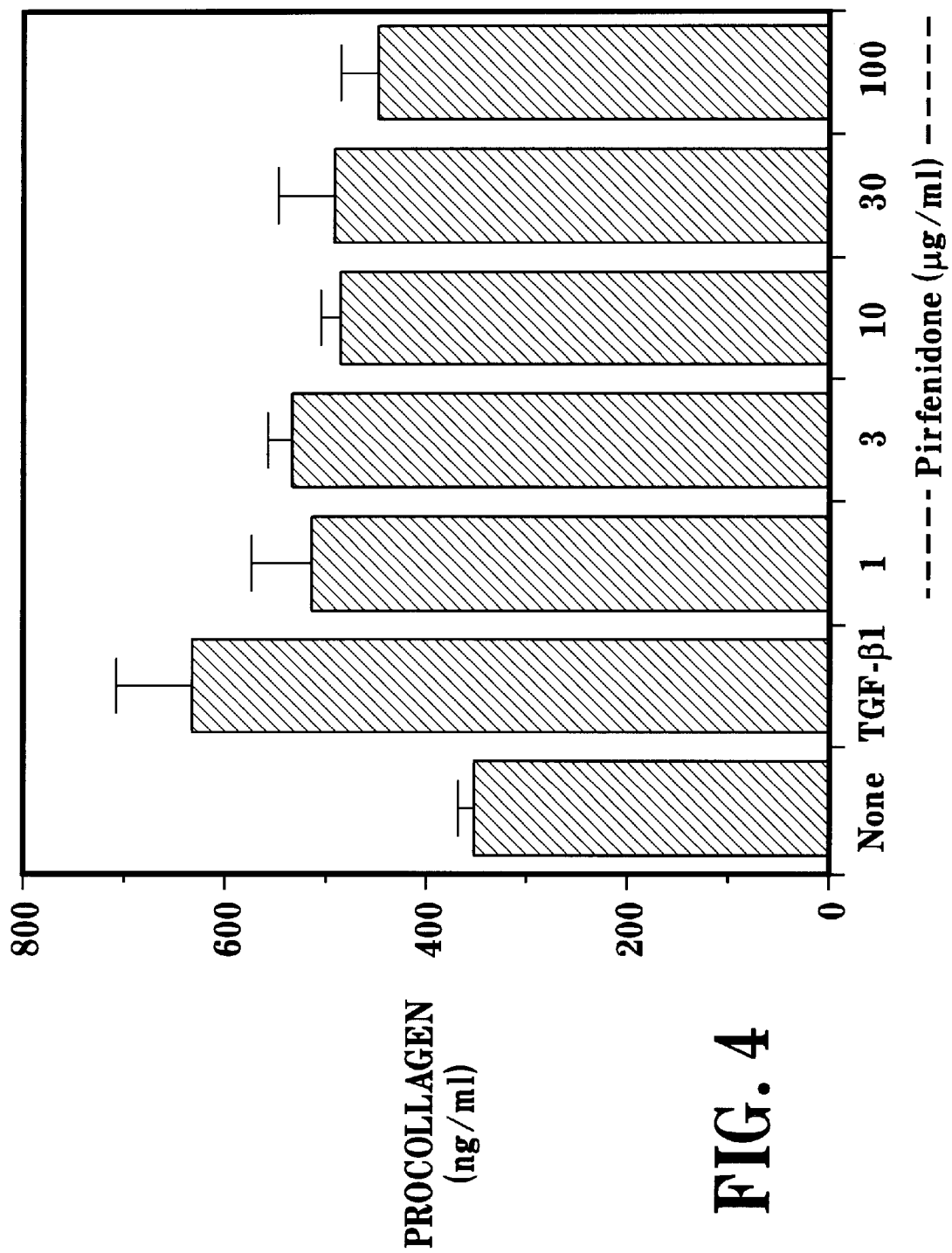

TGF-beta (10 nanograms/ml) increased procollagen content in conditioned medium from human prostate stromal cells as illustrated on FIG. 4. Pirfenidone (10–100 micrograms/ml) inhibited the increase in procollagen content in a concentration dependent manner.

Figure 5A:
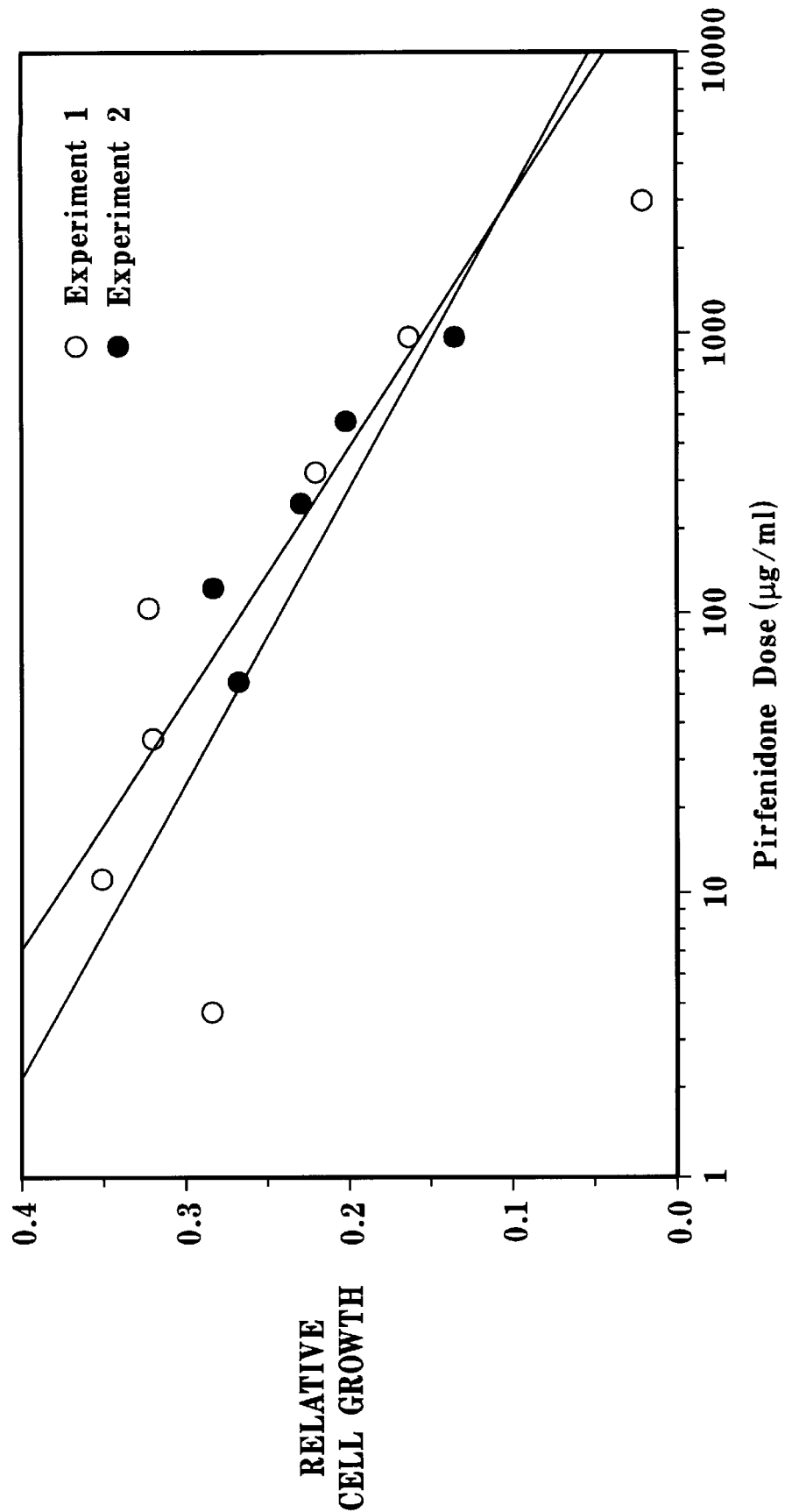
Figure 5B:
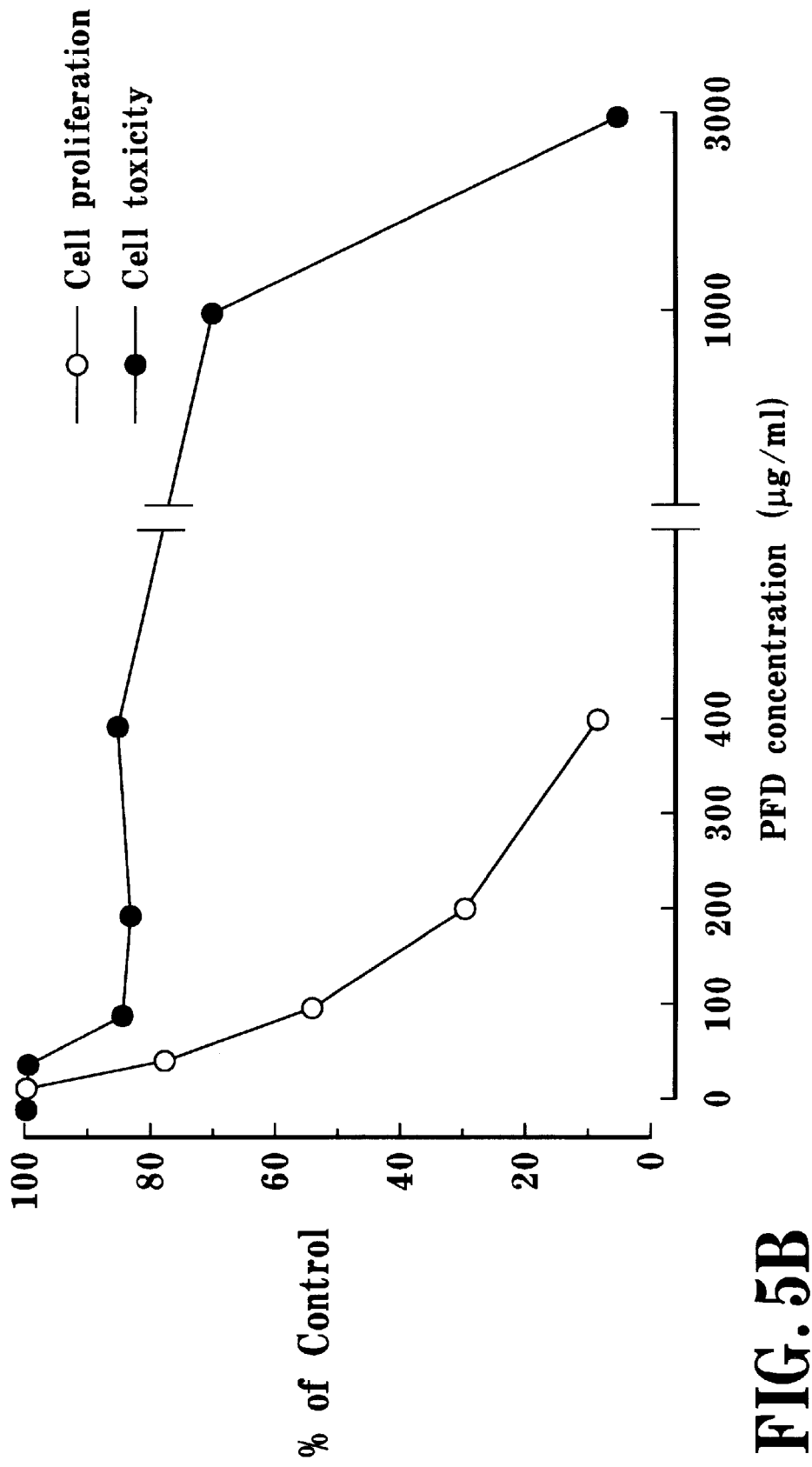

FIGS. 5A and 5B illustrate the effect of pirfenidone on proliferation of human lung fibroblast cells.

Figure 6:
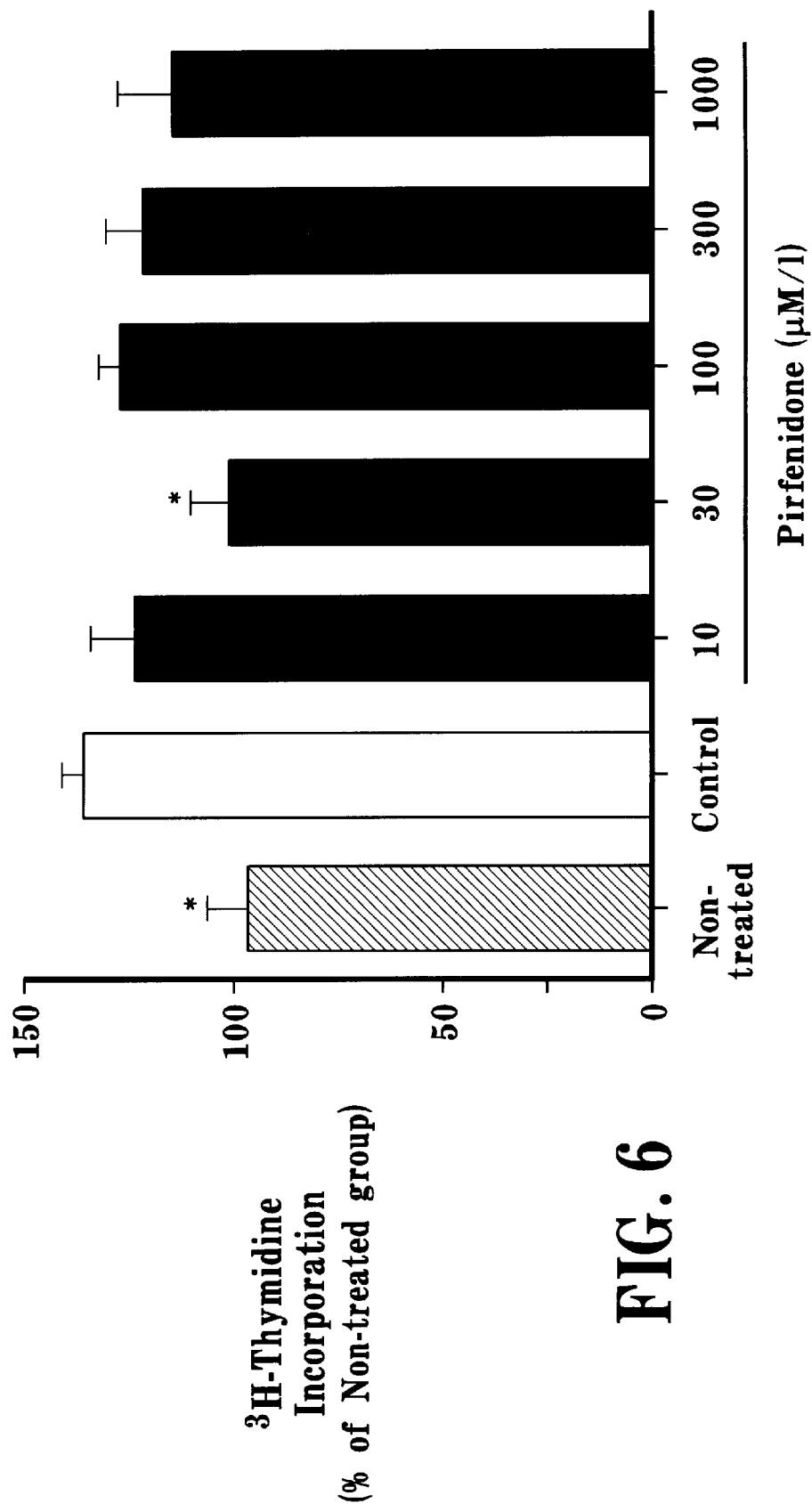

FIG. 6 illustrates the effect on proliferation of human lung fibroblast (WI38) cells. Pirfenidone inhibited the cell proliferation in a dose-dependent manner and ICso was calculated at approximately 100 mcg/ml. On the other hand, no apparent cell death was observed from vital staining even at 1,000 mcg/ml.

In addition to pirfenidone, N-substituted 2(1H) pyridones and N-substituted 3(1H) pyridones have been found or are believed to have efficacy in the prevention and treatment of disorders caused by enhanced proliferation and enhanced biosynthesis caused by cytokine growth factors.

The general structural formula for the 2 pyridones is:

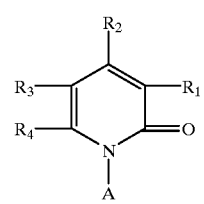

where: R1=alkyl group (CH3, C2H5, etc.); A is phenyl, thienyl, etc., or other aryl group. The alternate is for R3 to be the site of substitution of the alkyl group with R1 remaining as a hydrogen; R2 and R4 are, in every circumstance, hydrogens.

The general structural formual for the 3 pyridones is:

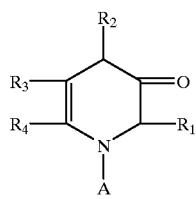

where: R2 or R3=alkyl group or hydrogen, as above; A is phenyl, thienyl, etc., or other aryl. R1 and R4 are hydrogen.

Examples of the 2 and 3 pyridones include:

5-Methyl-1-(3-nitrophenyl-2)-(1H) pyridone
5-Methyl-1-(4'-methoxyphenyl)-2-(1H) pyridone
5-Methyl-1-p-tolyl-2-(1H) pyridone
5-Methyl-1-(3'-trifluoromethylphenyl)-2-(1H) pyridone
1-(4'Chlorophenyl)-5-Methyl-2)-(1H) pyridone
5-Methyl-1-(2'-naphthyl)-2-(1H) pyridone
5-Methyl-1-(1'naphthyl)-2-(1H) pyridone
3-Methyl-1-phenyl-2-(1H) pyridone
3-Ethyl-1-phenyl-2-(1H) pyridone
6-Methyl-1-phenyl-2-(1H) pyridone
3,6-Dimethyl-1-phenyl-2-(1H) pyridone
5-Methyl-1-(2'-Thienyl)-2-(1H) pyridone
1-(2'-Furyl)-5-Methyl-2-(1H) pyridone
5-Methyl-1-(5'-quinolyl)-2-(1H) pyridone
5-Methyl-1-(4'-pyridyl)-2-(1H) pyridone
5-Methyl-1-(3'-pyridyl)-2-(1H) pyridone
5-Methyl-1-(2'-pyridyl)-2-(1H) pyridone
5-Methyl-1-(2'-quinolyl)-2-(1H) pyridone
5-Methyl-1-(4'-quinolyl)-2-(1H) pyridone
5-Methyl-1-(2'-thiazolyl)-2-(1H) pyridone
1-(2'-Imidazolyl)-5-Methyl-2-(1H) pyridone
5-Ethyl-1-phenyl-2-(1H) pyridone
1-Phenyl-2-(1H) pyridone
1-(4'-Nitrophenyl)-2-(1H) pyridone
1,3-Diphenyl-2-(1H) pyridone
1-Phenyl-3-(4 -chlorophenyl)-2-(1H) pyridone
1,3-Diphenyl-5-methyl-2-(1H) pyridone
3-(4'-Chlorophenyl)-5-Methyl-1-phenyl-2-(1H) pyridone
5-Methyl-3-phenyl-1-(2'-thienyl)-2-(1H) pyridone
5-Methyl-1-phenyl-3-(1H) pyridone
5-Methyl-1-(4'-methoxyphenyl)-3-(1H) pyridone
5-Methyl-1-p-tolyl-3-(1H) pyridone
1-(4'-Chlorophenyl)-5-methyl-3-(1H) pyridone
5-Methyl-1-(2'-naphthyl)-2-(1H) pyridone
4-Methyl-1-phenyl-3-(1H) pyridone
6-Methyl-1-phenyl-3-(1H) pyridone
5-Methyl-1(2'-Thienyl)-3-(1H) pyridone
1-(2'-Furyl)-5-methyl-3-(1H) pyridone
5-Methyl-1-(5'-quinolyl)-3-(1H) pyridone
5-Methyl-1-(3'-pyridyl)-3-(1H) pyridone
5-Methyl-1-(2'-pyridyl)-3-(1H) pyridone
5-Methyl-1-(2'-quinolyl)-3-(1H) pyridone
5-Ethyl-1-phenyl-3-(1H) pyridone
1-Phenyl-3-(1H) pyridone These compounds can be prepared using methods similar to those set forth in U.S. Pat. No. 3,839,346, issued Oct. 1, 1974, to Gadekar, and titled N-SUBSTITUTED PYRIDONE AND GENERAL METHOD FOR PREPARING PYRIDONES, the disclosure of which is incorporated by reference hereinto. That patent also describes use of some of those compounds in analgesic, anti-inflammatory, and antipyretic treatments. U.S. Pat. No. 3,974,281, issued Aug. 10, 1976; U.S. Pat. No. 4,042,699, issued Aug. 16, 1977; and U.S. Pat. No. 4,052,509, issued Oct. 4, 1988, all to Gadekar, describe further use of pirfenidone in lowering serum uric acid and glucose levels, treating upper respiratory inflammatory conditions, and treating inflammatory skin conditions, in humans and other animals. U.S. Pat. No. 5,310,562, issued May 10, 1994, to Margolin, and titled COMPOSITION AND METHOD FOR REPARATION AND PREVENTION OF FIBROTIC LESIONS, and copending U.S. application Ser. No. 08/243,058, by Margolin, and titled COMPOSITIONS AND METHODS FOR REPARATION AND PREVENTION OF FIBROTIC LESIONS disclose the use of the above compounds in the reparation and prevention of fibrotic lesions.

In laboratory animals, the oral effective dose in the various disorders mentioned above ranges from about 20 to about 150 mg/kg body weight per day in divided dosage. The wide range is due to the fact tha, in rodents (mice, rats, guinea pigs, hamsters, and rabbits), the drug is very rapidly metabolized and thus higher dosages are required. In dogs (who have a metabolic drug intake very similar to humans) and in humans, the daily dosage is in the range of 10–75 mg/kg body wieght per day in divided dosage.

The compositions of the present invention may be administered in forms consisting of capsules, tablets, powders, granules, syrups, aerosols, injectable fluids, pills, creams, ointments, inhalable fluids, eye drops, and suppositories.

It will thus be seen that the objects set forth above, among those elucidated in, or made apparent from, the preceding description, are efficiently attained and, since certain changes may be made in the above compositions and methods without departing from the scope of the invention, it is intended that all matter contained in the foregoing disclosure shall be interpreted as illustrative only and not in a limiting sense.

It is also to be understood that the following claims are intended to cover all of the generic and specific features of the invention herein described and all statements of the scope of the invention which, as a matter of language, might be said to fall therebetween

What is claimed is:

1. A method of prevention and treatment of disorders caused by enhanced proliferation and enhanced biosynthesis caused by cytokine growth factors, sensitive to the compounds below, in humans and other animals, in need thereof, comprising: administering to a human or other animal an effective dose of a pharmaceutical substance including an N-substituted 2(1H) pyridone having the following general structural formula:

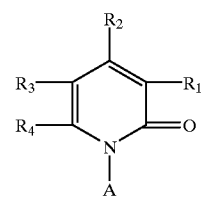

where; R1 is selected from the group consisting of (1) an alkyl group, with R3 hydrogen, and (2) hydrogen with R3 consisting of an alkyl group; A is an aryl group; and R2 and R4 are hydrogen;
and/or an N-substituted 3(1H) pyridone having the following general structural formula:

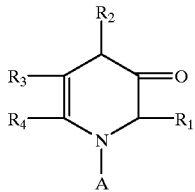

where: R2 is selected: from the group consisting of (1) an alkyl group, with R3 hydrogen and (2) hydrogen, with R3 consisting of an alkyl group; A is an aryl group; and R1 and R4 are hydrogen.

2. A method of prevention and treatment, as defined in claim 1, wherein said pharmaceutical substance includes one or more compounds selected from the group consisting of:

5-Methyl-1-phenyl-2-(1H) pyridone
5-Methyl-1-(3-nitrophenyl-2)-(1H) pyridone
5-Methyl-1-(4'-methoxyphenyl)-2-(1H) pyridone
5-Methyl-1-p-tolyl-2-(1H) pyridone
5-Methyl-1-(3'-trifluoromethylphenyl)-2-(1H) pyridone
1-(4'Chlorophenyl)-5-Methyl-2)-(1H) pyridone
5-Methyl-1-(2'-naphthyl)-2-(1H) pyridone
5-Methyl-1-(1'naphthyl)-2-(1H) pyridone
3-Methyl-1-phenyl-2-(1H) pyridone
3-Ethyl-1 phenyl-2-(1H) pyridone
6-Methyl-1-phenyl-2-(1H) pyridone
3,6-Dimethyl-1-phenyl-2-(1H) pyridone
5-Methyl-1-(2'-Thienyl)-2-(1H) pyridone
1-(2'-Furyl)-5-Methyl-2-(1H) pyridone
5-Methyl-1-(5'-quinolyl)-2-(1H) pyridone
5-Methyl-1-(4'-pyridyl)-2-(1H) pyridone
5-Methyl-1-(3'-pyridyl)-2-(1H) pyridone
5-Methyl-1-(2'-pyridyl)-2-(1H) pyridone
5-Methyl-1-(2'-quinolyl)-2-(1H) pyridone
5-Methyl-1-(4-quinolyl)-2-(1H) pyridone
5-Methyl-1-(2'-thiazolyl)-2-(1H) pyridone
1-(2'-Imidazolyl)-5-Methyl-2-(1H) pyridone
5-Ethyl-1-phenyl-2-(1H) pyridone
1-Phenyl-2-(1H) pyridone
1-(4'-Nitrophenyl)-2-(1H) pyridone
1,3-Diphenyl-2-(1H) pyridone
1-Phenyl-3-(4'-chlorophenyl)-2-(1H) pyridone
1,3-Diphenyl-5-methyl-2-(1H) pyridone
3-(4'-Chlorophenyl)-5-Methyl-1-phenyl-2-(1H) pyridone
5-Methyl-3-phenyl-1-(2'-thienyl)-2-(1H) pyridone
5-Methyl-1-phenyl-3-(1H) pyridone
5-Methyl-1-(4'-methoxyphenyl)-3-(1H) pyridone
5-Methyl-1-p-tolyl-3-(1H) pyridone
1-(4'-Chlorophenyl)-5-methyl-3-(1H) pyridone
5-Methyl-1-(2'-naphthyl)-3-(1H) pyridone
4-Methyl-1-phenyl-3-(1H) pyridone
6-Methyl-1-phenyl-3-(1H) pyridone
5-Methyl-1(2'-Thienyl)-3-(1H) pyridone
1-(2'-Furyl)-5-methyl-3-(1H) pyridone
5-Methyl-1-(5'-quinolyl)-3-(1H) pyridone
5-Methyl-1-(3'-pyridyl)-3-(1H) pyridone
5-Methyl-1-(2'-pyridyl)-3-(1H) pyridone
5-Methyl-1-(2'-quinolyl)-3-(1H) pyridone
5-Ethyl-1-phenyl-3-(1H) pyridone
1-Phenyl-3-(1H) pyridone.

3. A method of prevention and treatment, as defined in claim 1, wherein: said pharmaceutical substance is administered to a mammal in the amount of from about 20 to about 150 mg/kg body weight per day.

4. A method of prevention and treatment, as defined in claim 1, wherein: said pharmaceutical substance is administered in a form selected from the group consisting of: capsules, tablets, powders, granules, syrups, aerosols, injectable fluids, pills, creams, ointments, inhalable fluids, eye drops, and suppositories.

* * * * *